(12) United States Patent
Hashimoto et al.

(10) Patent No.: US 8,222,422 B2
(45) Date of Patent: Jul. 17, 2012

(54) CRYSTAL OF BENZIMIDAZOLE COMPOUND (75) Inventors: Hideo Hashimoto, Hikari (JP); Tadashi Urai, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 12/921,682

(22) PCT Filed: Mar. 9, 2009

(86) PCT No.: PCT/JP2009/054970
§ 371 (c)(1),
(2), (4) Date: Sep. 9, 2010

(87) PCT Pub. No.: WO2009/113696
PCT Pub. Date: Sep. 17, 2009

(65) Prior Publication Data
US 2011/0046183 A1    Feb. 24, 2011

(30) Foreign Application Priority Data

Mar. 10, 2008    (JP) ................................. 2008-059342

(51) Int. Cl.
C07D 401/00    (2006.01)
A61K 31/44    (2006.01)
(52) U.S. Cl. .................................... 546/273.7; 514/338
(58) Field of Classification Search ........................ None
See application file for complete search history.

(56) References Cited

U.S. PATENT DOCUMENTS

| | | | |
|---|---|---|---|
| 4,628,098 | A | 12/1986 | Nohara et al. |
| 5,840,737 | A | 11/1998 | Phillips |
| 6,462,058 | B1 | 10/2002 | Fujishima et al. |
| 6,664,276 | B2 | 12/2003 | Fujishima et al. |
| 6,939,971 | B2 | 9/2005 | Fujishima et al. |
| 7,169,799 | B2 | 1/2007 | Hashimoto et al. |
| 7,285,668 | B2 | 10/2007 | Hashimoto et al. |
| 7,339,064 | B2 | 3/2008 | Fujishima et al. |
| 2006/0057195 | A1 | 3/2006 | Nonomura et al. |

FOREIGN PATENT DOCUMENTS

| | | |
|---|---|---|
| DE | 40 35 455 | 5/1992 |
| EP | 0 174 726 | 3/1986 |
| EP | 0 302 720 | 2/1989 |
| EP | 1 293 507 | 3/2003 |
| EP | 1 552 833 | 7/2005 |
| WO | 92/08716 | 5/1992 |
| WO | 96/02535 | 2/1996 |
| WO | 96/17077 | 6/1996 |
| WO | 97/02261 | 1/1997 |
| WO | 98/21201 | 5/1998 |
| WO | 98/22118 | 5/1998 |
| WO | 98/28294 | 7/1998 |
| WO | 99/38512 | 8/1999 |
| WO | 99/38513 | 8/1999 |
| WO | 99/56698 | 11/1999 |
| WO | 2004/035052 | 4/2004 |
| WO | 2004/083200 | 9/2004 |
| WO | 2009/088857 | 7/2009 |

OTHER PUBLICATIONS

Bryn, et al., "Solid-State Chemistry of Drugs", Second Edition, SSCI, Inc., 91 pages, 1999.
U.S. Pharmacopia, #23, National Formulary #18 (1995), pp. 1843-1844.
Concise Encyclopedia Chemistry, Translated and revised by Mary Eagleson (1994), Walter de Gruyter: New York, pp. 872-873.
Rouhi, A. Maureen, "the Right Stuff", Journal C&E News (Feb. 24, 2003), pp. 32-35.
Katsuki, H. et al., "Determination of R(+)- and S(−)- Lansoprazole using Chiral Stationary-Phase Liquid Chromatography and Their Enantioselective Pharmacokinetics in Humans", Pharmaceutical Research, (1996), vol. 13, No. 4, pp. 611-615.
Curin, A. et al., "Study of Crystal Modifications of Lansoprazole using FT-IR Spectroscopy, Solid-State NMR Spectroscopy and FT-Raman Spectroscopy", Farm vestn (1997), vol. 48, pp. 290-291.
Vrecer, F. et al., "Study of Influence of Temperature and Grinding on the Crystalline State of Lansoprazole", Farm vestn, (1997), vol. 48, pp. 242-243.
Nagaya, H. et al., "Effects of the Enantiomers of Lansoprazole (AG-1979) on (H++K +)-ATPase Activity in Canine Gastric Microsomes and Acid Formation in Isolated Canine Parietal Cells", Biochemical Pharmacology, (1991), vol. 42, No. 10, pp. 1875-1878.
Hirschowitz, B. et al., "Long-Term Treatment with Lansoprazole for Patients with Zollinger-Ellison Syndrome", Aliment Pharmacol Ther (1996), vol. 10, pp. 507-522.
Figura, et al., "In-vitro activity of lansoprazole against *Helicobacter pylori*", Journal of Antimicrobial Chemotherapy, vol. 39, 1997, pp. 585-590.
Langtry, et al., "Lansoprazole", Drugs, vol. 54, No. 3, 1997, pp. 473-500.
Castell, et al., "Efficacy and Safety of lansoprazole in the treatment of erosive reflux esophagitis", The American Journal of Gastroenterology, vol. 91, No. 9, 1996, pp. 1749-1757.
Zimmermann, et al., "Lansoprazole: a comprehensive review", Pharmacotherapy, vol. 17, No. 2, 1997, pp. 308-326.
Katsuya, et al., "Lansoprazole reduces preoperative gastric fluid acidity and volume in children", Can J Anaesth., 1995, vol. 42, No. 6, pp. 467-472.
Borner, et al., "Separation of Lansoprazole Enantiomers in Human Serum by HPLC", Chromatographia, vol. 47, No. 3/4, Feb. 1998, pp. 171-175.
Arimori, et al., "Pharmacokinetic Differences Between Lansoprazole Enantiomers in Rats", J. Pharm. Pharmacol., 1998, vol. 50, pp. 1241-1245.
Landes, et al., "Clinical Pharmacokinetics of Lansoprazole", Clin. Pharmacokinet., 1995, vol. 28, No. 6, pp. 458-470.
"Experimental Organic Chemistry—Principle and Practice", Blackwell Scientific Publication 1989, pp. 127-132.

(Continued)

Primary Examiner — Janet Andres
Assistant Examiner — Heidi Reese
(74) Attorney, Agent, or Firm — Hamre, Schumann, Mueller & Larson, P.C.

(57) ABSTRACT

Provided is a crystal of (R)-2-[[[3-methyl-4-(2,2,2-trifluoroethoxy)-2-pyridinyl]methyl]sulfinyl]-1H-benzimidazole showing an X-ray powder diffraction pattern having characteristic peaks at interplanar spacings (d) of 10.06±0.2, 8.70±0.2, 6.57±0.2, 5.59±0.2 and 4.00±0.2 Angstroms. The present invention provides a stable antiulcer drug superior in the absorbability.

6 Claims, 6 Drawing Sheets

OTHER PUBLICATIONS

"Vogel's Textbook of Practical Organic Chemistry", Longman Scientific & Technical; Fifth Edition: 1989, pp. 141-142.

Byrn, "Solid State Chemistry of Drugs", Academic Press, 1982, pp. 10-13.

Opponent's Statement of Case filed in the matter of: Patent Application No. IL 145,996; *Teva Pharmaceutical Industries Ltd.* vs. *Takeda Pharmaceutical Company Limited*, Notice of Opposition filed Oct. 6, 2008, Opponent's Statement of Case filed Feb. 6, 2009—14 pages.

Robinson, Malcolm, Annals of Internal Medicine, vol. 124, vol. 10, pp. 859-867, 1996.

International Search Report issued in Application No. PCT/JP2009/054970, mailed May 18, 2009—3 pages.

CRYSTAL OF BENZIMIDAZOLE COMPOUND

TECHNICAL FIELD

The present invention relates to a crystal of a benzimidazole compound which shows an antiulcer action.

BACKGROUND OF THE INVENTION

2-[[[3-Methyl-4-(2,2,2-trifluoroethoxy)-2-pyridinyl]methyl]sulfinyl]-1H-benzimidazole or a salt thereof having an antiulcer action is reported in JP-A-61-50978, etc.

An anhydrous or hydrate crystal of optically active (R)-2-[[[3-methyl-4-(2,2,2-trifluoroethoxy)-2-pyridinyl]methyl]sulfinyl]-1H-benzimidazole is reported in WO2004/083200, WO01/87874, WO02/44167 and the like.

There is a demand for an antiulcer drug which is stable and superior in the absorbability.

DISCLOSURE OF THE INVENTION

The present inventors have conducted intensive studies and succeeded in producing (R) isomer of 2-[[[3-methyl-4-(2,2,2-trifluoroethoxy)-2-pyridinyl]methyl]sulfinyl]-1H-benzimidazole as a crystal having high stability and high solubility, and found that the crystal is sufficiently satisfactory as a pharmaceutical agent. In addition, it is known that a conventional anhydrous crystal of (R) isomer of 2-[[[3-methyl-4-(2,2,2-trifluoroethoxy)-2-pyridinyl]methyl]sulfinyl]-1H-benzimidazole is produced through a crystallization process. The present inventors have found that the anhydrous crystal of the present invention, which is a crystalline polymorph thereof, can be produced by an economical and convenient method including heating a known solvate crystal (including hydrate crystal) of an (R) isomer of 2-[[[3-methyl-4-(2,2,2-trifluoroethoxy)-2-pyridinyl]methyl]sulfinyl]-1H-benzimidazole or an amorphous (R) isomer of 2-[[[3-methyl-4-(2,2,2-trifluoroethoxy)-2-pyridinyl]methyl]sulfinyl]-1H-benzimidazole, without going through general crystallization processes. Based on such finding, they have completed the present invention.

Accordingly, the present invention relates to:
(1) a crystal of (R)-2-[[[3-methyl-4-(2,2,2-trifluoroethoxy)-2-pyridinyl]methyl]sulfinyl]-1H-benzimidazole wherein the powder X-ray diffraction analysis pattern has characteristic peaks at interplanar spacings (d) of 10.06±0.2, 8.70±0.2, 6.57±0.2, 5.59±0.2 and 4.00±0.2 Angstrom,
(2) a pharmaceutical agent comprising the crystal of the aforementioned (1),
(3) the pharmaceutical agent of the aforementioned (2), which is an agent for the prophylaxis or treatment of peptic ulcer, Zollinger-Ellison syndrome, gastritis, reflux esophagitis, symptomatic gastroesophageal reflux disease (Symptomatic GERD), Barrett's esophagus, functional dyspepsia, gastric cancer, stomach MALT lymphoma, ulcer caused by a nonsteroidal anti-inflammatory agent, or hyperacidity or ulcer due to postoperative stress; or an inhibitor of upper gastrointestinal hemorrhage due to peptic ulcer, acute stress ulcer, hemorrhagic gastritis or invasive stress,
(4) a method of treating or preventing peptic ulcer, Zollinger-Ellison syndrome, gastritis, reflux esophagitis, symptomatic gastroesophageal reflux disease (Symptomatic GERD), Barrett's esophagus, functional dyspepsia, gastric cancer, stomach MALT lymphoma, ulcer caused by a nonsteroidal anti-inflammatory agent, or hyperacidity or ulcer due to postoperative stress; or a method of inhibiting upper gastrointestinal hemorrhage due to peptic ulcer, acute stress ulcer, hemorrhagic gastritis or invasive stress, which comprises administering an effective amount of the crystal of the aforementioned (1) to a mammal,
(5) use of the crystal of the aforementioned (1) for the production of an agent for the prophylaxis or treatment of peptic ulcer, Zollinger-Ellison syndrome, gastritis, reflux esophagitis, symptomatic gastroesophageal reflux disease (Symptomatic GERD), Barrett's esophagus, functional dyspepsia, gastric cancer, stomach MALT lymphoma, ulcer caused by a nonsteroidal anti-inflammatory agent, or hyperacidity or ulcer due to postoperative stress; or an inhibitor of upper gastrointestinal hemorrhage due to peptic ulcer, acute stress ulcer, hemorrhagic gastritis or invasive stress,
(6) a production method of a crystal of (R)-2-[[[3-methyl-4-(2,2,2-trifluoroethoxy)-2-pyridinyl]methyl]sulfinyl]-1H-benzimidazole, comprising heating amorphous (R)-2-[[[3-methyl-4-(2,2,2-trifluoroethoxy)-2-pyridinyl]methyl]sulfinyl]-1H-benzimidazole or a solvate crystal of (R)-2-[[[3-methyl-4-(2,2,2-trifluoroethoxy)-2-pyridinyl]methyl]sulfinyl]-1H-benzimidazole to not lower than about 71° C., and the like.

Since the crystal of the present invention has a superior antiulcer activity, a gastric acid secretion-inhibiting action, a mucosa-protecting action, an anti-*Helicobacter pylori* activity and the like, as well as low toxicity, it is useful as a pharmaceutical product. Moreover, since the crystal of the present invention has high stability and high solubility, when it is orally administered, it achieves superior absorbability and rapid expression of action as compared to racemate and known optical isomer crystals. In addition, when the crystal of the present invention is administered, it shows higher Cmax and greater AUC as compared to racemate, and shows an extended duration of the action because it becomes likely to resist metabolism because of the increased protein binding ratio and the like. Therefore, the crystal is useful as a pharmaceutical product with a small dose and a fewer side effects. Furthermore, the crystal of the present invention can be obtained by merely heating a solvate crystal (including hydrate crystal) or an amorphous form of 2-[[[3-methyl-4-(2,2,2-trifluoroethoxy)-2-pyridinyl]methyl]sulfinyl]-1H-benzimidazole, without a crystallization process necessary for the production of a known anhydrous crystal of an (R) isomer thereof. Thus, the operation is convenient and an economical production is available.

DETAILED DESCRIPTION OF THE INVENTION

The crystal of (R)-2-[[[3-methyl-4-(2,2,2-trifluoroethoxy)-2-pyridinyl]methyl]sulfinyl]-1H-benzimidazole (hereinafter sometimes to be abbreviated as (R)-lansoprazole) of the present invention may be a solvate such as hydrate and the like, or may be an ansolvate.

Here, the enantiomeric excess of (R)-lansoprazole of the present invention is, for example, not less than about 80% ee, preferably not less than about 90% ee.

Examples of the "hydrate" include 0.5 hydrate to 5.0 hydrate. Among these, 0.5 hydrate, 1.0 hydrate, 1.5 hydrate, 2.0 hydrate and 2.5 hydrate are preferable. Particularly preferred are 0.5 hydrate, 1.0 hydrate and 1.5 hydrate.

The (R)-lansoprazole or a hydrate thereof of the present invention may be a deuterated form.

In addition, the crystal of (R)-lansoprazole of the present invention may be a solvate other than hydrates.

Examples of the solvate crystal of (R)-lansoprazole include alcohol solvate crystals such as methanol solvate crystal, ethanol solvate crystal and the like (preferably $C_{1-6}$ alcohol solvate crystal), organic solvent hydrate crystal to which water and organic solvent are added (e.g., alcohol hydrate crystals such as methanol hydrate, ethanol hydrate, etc., preferably $C_{1-6}$ alcohol hydrate crystal) and the like.

The crystal of the present invention can be produced by crystal transformation of amorphous (R)-lansoprazole or a solvate crystal of (R)-lansoprazole (including hydrate crystal, hereinafter the same).

The crystal transformation is a phenomenon where a crystal structure changes when the temperature or pressure exceeds a certain level.

Examples of the method of crystal transformation include "crystallization from a solution" to be mentioned below, as well as, for example, a transpiration method (in which a known crystal is dissolved in a solvent and, after filtration, the solvent is evaporated under atmospheric conditions), a slurry method (in which a known crystal is added to a solvent such that excess solid remains therein to give a suspension, the suspension is stirred at atmospheric temperature or under heating and the solid is collected by filtration), and methods such as drying under reduced pressure, pulverization, pressurization, heating and the like.

To obtain the crystal of the present invention, a method including heating amorphous (R)-lansoprazole or a solvate crystal of (R)-lansoprazole is particularly preferable from among the above-mentioned methods.

The method of heating is not particularly specified and, for example, amorphous (R)-lansoprazole or a solvate crystal of (R)-lansoprazole is heated to about 71° C. or above, preferably about 71° C. to about 140° C., more preferably about 75° C. to about 120° C., particularly preferably about 80° C. to about 110° C., using a heating apparatus.

As the heating apparatus, for example, water bath, oil bath, immersion heater, mantle heater, chamber dryer, filter dryer, vibrating dryer, double-cone dryer, Nauta mixer, agitated cylinder dryer, fluidized bed dryer, pneumatic conveying dryer, infrared dryer, microwave dryer and the like can be used.

Along with heating, pressurization, depressurization, atmosphere pressure, air flow, infrared irradiation, microwave irradiation and the like may be employed.

The above-mentioned "depressurization" means placement under the conditions of less than the atmosphere pressure, preferably not more than about 100 mmHg, more preferably about 0 to 50 mmHg.

To perform drying along with heating, depressurization or air flow may be employed, or simple heating may be employed. Particularly, a method including heating under reduced pressure to simultaneously perform drying during heating, or a method including heating alone is preferable.

The aforementioned amorphous (R)-lansoprazole can be obtained by the method described in WO2004/035052 or WO2004/083200.

Specifically, it can be produced by preserving a wet crystal of (R)-lansoprazole (preferably hydrate, more preferably 0.5 hydrate or 1.5 hydrate) at or heating same to, for example, about 50° C. to about 70° C.

Examples of the solvate crystal of the aforementioned (R)-lansoprazole include hydrate crystals such as 0.5 hydrate to 5.0 hydrate and the like (e.g., 0.5 hydrate, 1.0 hydrate, 1.5 hydrate, 2.0 hydrate, 2.5 hydrate, etc.); alcohol solvate crystals such as methanol solvate, ethanol solvate and the like; alcohol hydrate crystals such as methanol hydrate, ethanol hydrate, etc., and the like.

As the solvate crystal, hydrate crystals such as 0.5 hydrate to 5.0 hydrate and the like are preferable, and 0.5 hydrate, 1.0 hydrate and 1.5 hydrate are particularly preferable.

In addition, (R)-lansoprazole and hydrates thereof may be in a deuterated form.

The crystal of solvate (e.g., hydrate) of (R)-lansoprazole can be produced according to WO2004/083200 or WO01/87874.

As methods of crystallizing a solvate, methods known per se, for example, crystallization from solution, crystallization from vapor, and crystallization from molten form can be employed.

Methods of the "crystallization from solution" include, for example, a concentration method, a slow cooling method, a reaction method (diffusion method, electrolysis method), a hydrothermal growth method, a fusing agent method, and so forth. Solvents to be used include, for example, aromatic hydrocarbons (e.g., benzene, toluene, xylene, etc.), halogenated hydrocarbons (e.g., dichloromethane, chloroform, etc.), saturated hydrocarbons (e.g., hexane, heptane, cyclohexane, etc.), ethers (e.g., diethyl ether, diisopropyl ether, tetrahydrofuran, dioxane, etc.), nitriles (e.g., acetonitrile, etc.), ketones (e.g., acetone, etc.), sulfoxides (e.g., dimethylsulfoxide, etc.), acid amides (e.g., N,N-dimethylformamide, etc.), esters (e.g., ethyl acetate, etc.), alcohols (e.g., methanol, ethanol, isopropyl alcohol, etc.), water, and so forth. These solvents may be used singly or in a mixture of two or more kinds at an appropriate ratio (e.g., 1:1 to 1:100).

For example, when a hydrate crystal is to be obtained, water, a mixture of water and other solvent, and the like are used; when an alcohol solvate crystal is to be obtained, alcohol or a mixture of alcohol and other solvent is used; and when an alcohol hydrate crystal is to be obtained, a mixture of alcohol and water or a mixture of alcohol, water and other solvent is used.

Methods of the "crystallization from vapor" include, for example, a gasification method (sealed tube method, gas stream method), a gas phase reaction method, a chemical transportation method, and so forth.

Methods of the "crystallization from molten form" include, for example, a normal freezing method (pulling-up method, temperature gradient method, Bridgman method), a zone melting method (zone leveling method, float zone method), a special growth method (VLS method, liquid phase epitaxis method), and so forth.

For analyzing the crystal obtained, X-ray diffraction crystallographic analysis is commonly used. In addition, crystal orientation can also be determined by a mechanical method, an optical method (e.g., FT-Raman spectrum, solid NMR spectrum), etc.

The peak of the spectrum obtained by the above-mentioned analysis method inevitably contains a certain measurement error by its nature. A crystal with a spectrum peak within the error range is also encompassed in the crystal of the present invention. For example, "±0.2" in the interplanar spacing (d) of powder X-ray diffraction means that the error is tolerable.

The crystal of the present invention produced by the aforementioned method is a novel crystal showing an X-ray powder diffraction pattern having characteristic peaks at interplanar spacings (d) of 10.06±0.2, 8.70±0.2, 6.57±0.2, 5.59±0.2 and 4.00±0.2 Angstroms, by powder X-ray diffraction, and is preferably a crystal of ansolvate (anhydrate).

The crystal of the present invention is preferably a crystal showing an X-ray powder diffraction pattern having characteristic peaks at interplanar spacings (d) of 10.06±0.2, 8.70±0.2, 6.57±0.2, 5.73±0.2, 5.59±0.2, 4.83±0.2, 4.38±0.2, 4.00±0.2, 3.93±0.2 and 3.73±0.2 Angstroms.

The crystal of the present invention is more preferably a crystal showing X-ray powder diffraction pattern having characteristic peaks at interplanar spacings (d) of 9.95±0.2, 8.65±0.2, 6.54±0.2, 5.56±0.2 and 3.98±0.2 Angstroms.

The crystal of the present invention is more preferably a crystal showing an X-ray powder diffraction pattern having characteristic peaks at interplanar spacings (d) of 9.95±0.2, 8.63±0.2, 6.53±0.2, 5.56±0.2 and 3.90±0.2 Angstroms.

The crystal of the present invention is more preferably a crystal showing an X-ray powder diffraction pattern having characteristic peaks at interplanar spacings (d) of 10.04±0.2, 8.72±0.2, 6.58±0.2, 5.60±0.2 and 3.99±0.2 Angstroms.

The crystal of the present invention is more preferably a crystal showing an X-ray powder diffraction pattern having characteristic peaks at interplanar spacings (d) of 9.99±0.2, 8.58±0.2, 6.53±0.2, 5.55±0.2 and 3.98±0.2 Angstroms.

The crystal of the present invention is more preferably a crystal showing an X-ray powder diffraction pattern having characteristic peaks at interplanar spacings (d) of 10.11±0.2, 8.77±0.2, 6.60±0.2, 5.61±0.2 and 4.01±0.2 Angstroms.

Thus obtained crystal of the present invention is useful as a pharmaceutical since it shows an excellent antiulcer action, a gastric acid secretion-inhibiting action, a mucosa-protecting action, an anti-*Helicobacter pylori* action, and the like, as well as low toxicity. Moreover, since the crystal of the present invention is superior in the stability, it can be handled easily and can be processed into a solid pharmaceutical composition with good reproducibility. In addition, when the crystal of the present invention is orally administered, the action is rapidly expressed since it is superior in the dissolution property and absorbability. Furthermore, when the crystal of the present invention is administered, it shows higher Cmax (maximum blood concentration) and greater AUC (area under the concentration-time curve), and shows an extended duration of the action because it becomes likely to resist metabolism because of the increased protein binding ratio and the like. Therefore, the crystal is useful as a pharmaceutical product with a small dose and a fewer side effects. Furthermore, the crystal of the present invention can be obtained by merely heating a solvate (including hydrate crystal) or an amorphous form of 2-[[[3-methyl-4-(2,2,2-trifluoroethoxy)-2-pyridinyl]methyl]sulfinyl]-1H-benzimidazole, without a crystallization process necessary for the production of a known anhydrous crystal of an (R) isomer thereof. Thus, the operation is convenient and an economical production is available.

The crystal of the present invention is useful for mammals (e.g., humans, monkeys, sheep, bovines, horses, dogs, cats, rabbits, rats, mice, etc.) for the treatment or prophylaxis of peptic ulcer (e.g., gastric ulcer, duodenal ulcer, anastomotic ulcer etc.); Zollinger-Ellison syndrome; gastritis; erosive esophagitis; reflux esophagitis such as erosive reflux esophagitis and the like; symptomatic gastroesophageal reflux disease (symptomatic GERD) such as non-erosive reflux disease or gastroesophageal reflux disease free of esophagitis and the like; Barrett's esophagus; functional dyspepsia; gastric cancer (including gastric cancer associated with promoted production of interleukin-1β due to gene polymorphism of interleukin-1); stomach MALT lymphoma; ulcer caused by a nonsteroidal anti-inflammatory agent or hyperacidity and ulcer due to postoperative stress; gastric hyperacidity; upper gastrointestinal hemorrhage due to peptic ulcer, ulcer caused by a nonsteroidal anti-inflammatory agent or ulcer due to postoperative stress, acute stress ulcer, hemorrhagic gastritis or invasive stress (e.g. stress caused by major surgery requiring postoperative intensive management, and cerebrovascular disorder, head trauma, multiple organ failure and extensive burn, each requiring intensive treatment) and the like; pre-anesthetic administration, eradication of *Helicobacter pylori* or eradication assistance and the like.

As used herein, the above-mentioned reflux esophagitis and symptomatic gastroesophageal reflux disease (symptomatic GERD) are sometimes collectively referred to simply as GERD.

The crystal of the present invention is of low toxicity and can be safely administered orally or non-orally (e.g., topical, rectal and intravenous administration, etc.), as such or in the form of pharmaceutical compositions formulated with a pharmacologically acceptable carrier, e.g., tablets (including sugar-coated tablets and film-coated tablets), powders, granules, capsules (including soft capsules), orally disintegrating tablets, orally disintegrating films, liquids, injectable preparations, suppositories, sustained-release preparations and patches, in accordance with a commonly known method.

The content of the crystal in the pharmaceutical composition of the present invention is about 0.01 to 100% by weight relative to the entire composition. Varying depending on subject of administration, route of administration, target disease etc., its dose is normally about 0.5 to 1,500 mg/day, preferably about 5 to 150 mg/day, based on the active ingredient, for example, when it is orally administered as an antiulcer agent to an adult human (60 kg). The crystal of the present invention may be administered once daily or in 2 to 3 divided portions per day.

Pharmacologically acceptable carriers that may be used to produce the pharmaceutical composition of the present invention include various organic or inorganic carrier substances in common use as pharmaceutical materials, including excipients, lubricants, binders, disintegrants, water-soluble polymers and basic inorganic salts for solid preparations; and solvents, solubilizing agents, suspending agents, isotonizing agents, buffers and soothing agents for liquid preparations. Other ordinary pharmaceutical additives such as preservatives, antioxidants, colorants, sweetening agents, souring agents, bubbling agents and flavorings may also be used as necessary.

Such "excipients" include, for example, lactose, sucrose, D-mannitol, starch, cornstarch, crystalline cellulose, light anhydrous silicic acid and titanium oxide.

Such "lubricants" include, for example, magnesium stearate, sucrose fatty acid esters, polyethylene glycol, talc and stearic acid.

Such "binders" include, for example, hydroxypropyl cellulose, hydroxypropylmethyl cellulose, crystalline cellulose, α-starch, polyvinylpyrrolidone, gum arabic powder, gelatin, pullulan and low-substitutional hydroxypropyl cellulose.

Such "disintegrants" include (1) crosspovidone, (2) what is called super-disintegrants such as crosscarmellose sodium (FMC-Asahi Chemical) and carmellose calcium (Gotoku Yakuhin), (3) sodium carboxymethyl starch (e.g., product of Matsutani Chemical), (4) low-substituted hydroxypropyl cellulose (e.g., product of Shin-Etsu Chemical), (5) cornstarch, and so forth. Said "crospovidone" may be any crosslinked polymer having the chemical name 1-ethenyl-2-pyrrolidinone homopolymer, including polyvinylpolypyrrolidone (PVPP) and 1-vinyl-2-pyrrolidinone homopolymer, and is exemplified by Colidon CL (produced by BASF), Polyplasdon XL (produced by ISP), Polyplasdon XL-10 (produced by ISP) and Polyplasdon INF-10 (produced by ISP).

Such "water-soluble polymers" include, for example, ethanol-soluble water-soluble polymers [e.g., cellulose derivatives such as hydroxypropyl cellulose (hereinafter also referred to as HPC), polyvinylpyrrolidone] and ethanol-insoluble water-soluble polymers [e.g., cellulose derivatives such as hydroxypropylmethyl cellulose (hereinafter also referred to as HPMC), methyl cellulose and carboxymethyl cellulose sodium, sodium polyacrylate, polyvinyl alcohol, sodium alginate, guar gum].

Such "basic inorganic salts" include, for example, basic inorganic salts of sodium, potassium, magnesium and/or calcium. Preferred are basic inorganic salts of magnesium and/or calcium. More preferred are basic inorganic salts of magnesium. Such basic inorganic salts of sodium include, for example, sodium carbonate, sodium hydrogen carbonate, disodium hydrogenphosphate, etc. Such basic inorganic salts of potassium include, for example, potassium carbonate, potassium hydrogen carbonate, etc. Such basic inorganic salts of magnesium include, for example, heavy magnesium carbonate, magnesium carbonate, magnesium oxide, magnesium hydroxide, magnesium aluminometasilicate, magnesium silicate, magnesium aluminate, synthetic hydrotalcite [$Mg_6Al_2(OH)_{16}.CO_3.4H_2O$], aluminum magnesium hydroxide, and so forth. Among others, preferred is heavy magnesium carbonate, magnesium carbonate, magnesium oxide, magnesium hydroxide, etc. Such basic inorganic salts of calcium include, for example, precipitated calcium carbonate, calcium hydroxide, etc.

Such "solvents" include, for example, water for injection, alcohol, propylene glycol, macrogol, sesame oil, corn oil and olive oil.

Such "solubilizing agents" include, for example, polyethylene glycol, propylene glycol, D-mannitol, benzyl benzoate, ethanol, trisaminomethane, cholesterol, triethanolamine, sodium carbonate and sodium citrate.

Such "suspending agents" include, for example, surfactants such as stearyltriethanolamine, sodium lauryl sulfate, laurylaminopropionic acid, lecithin, benzalkonium chloride, benzethonium chloride and glyceryl monostearate; and hydrophilic polymers such as polyvinyl alcohol, polyvinylpyrrolidone, carboxymethyl cellulose sodium, methyl cellulose, hydroxymethyl cellulose, hydroxyethyl cellulose and hydroxypropyl cellulose.

Such "isotonizing agents" include, for example, glucose, D-sorbitol, sodium chloride, glycerol and D-mannitol.

Such "buffers" include, for example, buffer solutions of phosphates, acetates, carbonates, citrates etc.

Such "soothing agents" include, for example, benzyl alcohol.

Such "preservatives" include, for example, p-oxybenzoic acid esters, chlorobutanol, benzyl alcohol, phenethyl alcohol, dehydroacetic acid and sorbic acid.

Such "antioxidants" include, for example, sulfites, ascorbic acid and α-tocopherol.

Such "colorants" include, for example, food colors such as Food Color Yellow No. 5, Food Color Red No. 2 and Food Color Blue No. 2; and food lake colors and red ferric oxide.

Such "sweetening agents" include, for example, saccharin sodium, dipotassium glycyrrhetinate, aspartame, stevia and thaumatin.

Such "souring agents" include, for example, citric acid (anhydrous citric acid), tartaric acid and malic acid.

Such "bubbling agents" include, for example, sodium bicarbonate.

Such "flavorings" may be synthetic substances or naturally occurring substances, and include, for example, lemon, lime, orange, menthol and strawberry.

The crystal of the present invention may be prepared as a preparation for oral administration in accordance with a commonly known method, by, for example, compression-shaping it in the presence of an excipient, a disintegrant, a binder, a lubricant, or the like, and subsequently coating it as necessary by a commonly known method for the purpose of taste masking, enteric dissolution or sustained release. For an enteric preparation, an intermediate layer may be provided by a commonly known method between the enteric layer and the drug-containing layer for the purpose of separation of the two layers.

For preparing the crystal of the present invention as an orally disintegrating tablet, available methods include, for example, a method in which a core containing crystalline cellulose and lactose is coated with the crystal of the present invention and a basic inorganic salt, and is further coated with a coating layer containing a water-soluble polymer, to give a composition, which is coated with an enteric coating layer containing polyethylene glycol, further coated with an enteric coating layer containing triethyl citrate, still further coated with an enteric coating layer containing polyethylene glycol, and still yet further coated with mannitol, to give fine granules, which are mixed with additives and shaped. The above-mentioned "enteric coating layer" includes, for example, aqueous enteric polymer substrates such as cellulose acetate phthalate (CAP), hydroxypropylmethyl cellulose phthalate, hydroxymethyl cellulose acetate succinate, methacrylic acid copolymers [e.g., Eudragit L30D-55 (trade name; produced by Rohm), Colicoat MAE30DP (trade name; produced by BASF), Polykid PA30 (trade name; produced by San-yo Chemical)], carboxymethylethyl cellulose and shellac; sustained-release substrates such as methacrylic acid polymers [e.g., Eudragit NE30D (trade name), Eudragit RL30D (trade name), Eudragit RS30D (trade name), etc.]; water-soluble polymers; plasticizers such as triethyl citrate, polyethylene glycol, acetylated monoglycerides, triacetine and castor oil; and mixtures thereof. The above-mentioned "additive" includes, for example, water-soluble sugar alcohols (e.g., sorbitol, mannitol, maltitol, reduced starch saccharides, xylitol, reduced paratinose, erythritol, etc.), crystalline cellulose [e.g., Ceolas KG 801, Avicel PH 101, Avicel PH 102, Avicel PH 301, Avicel PH 302, Avicel RC-591 (crystalline cellulose carmellose sodium)], low-substituted hydroxypropyl cellulose [e.g., LH-22, LH-32, LH-23, LH-33 (Shin-Etsu Chemical) and mixtures thereof]; binders, souring agents, bubbling agents, sweetening agents, flavorings, lubricants, colorant s, stabilizers, excipients, disintegrants etc. are also used.

The crystal of the present invention is preferably formulated into a solid dosage form such as capsule and the like according to, for example, WO2004/035020. To be specific, preferred is a capsule comprising
(i) a tablet, granule or fine granule in which the release of (R)-lansoprazole is controlled; said tablet, granule or fine granule comprises a core particle containing (R)-lansoprazole, and a pH-dependently soluble release-controlled coating-layer which comprises one kind of polymeric substance or a mixture of two or more kinds of polymeric substances having different release properties selected from the group consisting of hydroxypropylmethyl cellulose phthalate, cellulose acetate phthalate, carboxymethylethyl cellulose, methyl methacrylate-methacrylic acid copolymer, methacrylic acid-ethyl acrylate copolymer, methacrylic acid-methyl acrylate-methyl methacrylate copolymer, hydroxypropyl cellulose acetate succinate, polyvinyl acetate phthalate and shellac; said polymeric substance is soluble in the pH range of 6.0 to 7.5, and
(ii) a tablet, granule or fine granule comprising a core particle containing (R)-lansoprazole and enteric coat which is dissolved, thereby an active ingredient being released in the pH range of no less than 5.0, less than 6.0, and the like.

The crystal of the present invention may be used in combination with 1 to 3 other active ingredients.

Such "other active ingredients" include, for example, anti-*Helicobacter pylori* activity substances, imidazole compounds, bismuth salts, quinolone compounds, and so forth. Of these substances, preferred are anti-*Helicobacter pylori* action substances, imidazole compounds etc.

Such "anti-*Helicobacter pylori* action substances" include, for example, antibiotic penicillins (e.g., amoxicillin, benzylpenicillin, piperacillin, mecillinam, etc.), antibiotic cefems (e.g., cefixime, cefaclor, etc.), antibiotic macrolides (e.g., erythromycin, clarithromycin. etc.), antibiotic tetracyclines (e.g., tetracycline, minocycline, streptomycin, etc.), antibiotic aminoglycosides (e.g., gentamicin, amikacin, etc.), imipenem, and so forth. Of these substances, preferred are antibiotic penicillins, antibiotic macrolides etc. Such "imidazole compounds" include, for example, metronidazole, miconazole, etc. Such "bismuth salts" include, for example, bismuth acetate, bismuth citrate, etc. Such "quinolone compounds" include, for example, ofloxacin, ciploxacin, etc.

Such "other active ingredients" and the crystal of the present invention may also be used in combination as a mixture prepared as a single pharmaceutical composition [e.g., tablets, powders, granules, capsules (including soft capsules), liquids, injectable preparations, suppositories, sustained-release preparations, etc.], in accordance with a commonly known method, and may also be prepared as separate preparations and administered to the same subject simultaneously or at a time interval.

EXAMPLES

The present invention is hereinafter described in more detail by means of, but is not limited to, the following Reference Examples, Examples and Analytical Examples.

In the following Reference Examples, Examples and Analytical Examples, the room temperature indicates about 15° C. to 30° C.

$^1$H-NMR was measured by Bruker DPX-300 (300 MHz) using CDCl$_3$ as a solvent and the chemical shift δ (ppm) from tetramethylsilane as an internal standard is shown.

IR was measured by HORIBA FT-210.

Water content was measured by Hiranuma Sangyo Corporation Aquacounter AQU-7.

Optical purity was measured by HPLC using a chiral column (column: Shinwa Kako ULTRON ES-Ph CD 6.0 mmφ× 150 mm, temperature: about 25° C., mobile phase: 0.02 mol/L aqueous phosphoric acid solution (pH 7.0) (*)/acetonitrile=3/2, flow rate: 1.0 mL/min, detection wavelength: 285 nm).

(*) prepared from aqueous disodium hydrogenphosphate 12-water solution and aqueous potassium dihydrogenphosphate solution.

Chemical purity was measured by HPLC (column: Shiseido CAPCELLPAK C18 SG120 5 μm 4.6 mmφ×250 mm, temperature: about 25° C., mobile phase: water/acetonitrile/triethylamine=50/50/1 (adjusted to pH7.0 with phosphoric acid), flow rate: 1.0 mL/min, detection wavelength: 285 nm).

Residual rate was measured by HPLC (YMC-Pack AQ-302 ODS 4.6 mm i.d.×150 mm, temperature: about 25° C., mobile phase: (A) water (B) acetonitrile:water:triethylamine=160:40:1, gradient program, detection wavelength: 285 nm).

Powder X-ray diffraction was measured by X-ray Powder Diffractometer Rigaku RINT2000 (ultima+).

Differential scanning calorimetry (DSC) was measured within the range of 27° C. to 180° C. at a temperature rise rate of 5° C./min and using differential scanning calorimeter (SEIKO DSC220C).

Heating was performed in an oil bath (RIKO MH-5D) or using a chamber dryer (YAMATO DP41).

Other symbols in the present description mean the following.
s: singlet
d: doublet
q: quartet
m: multiplet
bs: broad singlet
J: coupling constant Reference Example 1

Figure 1:
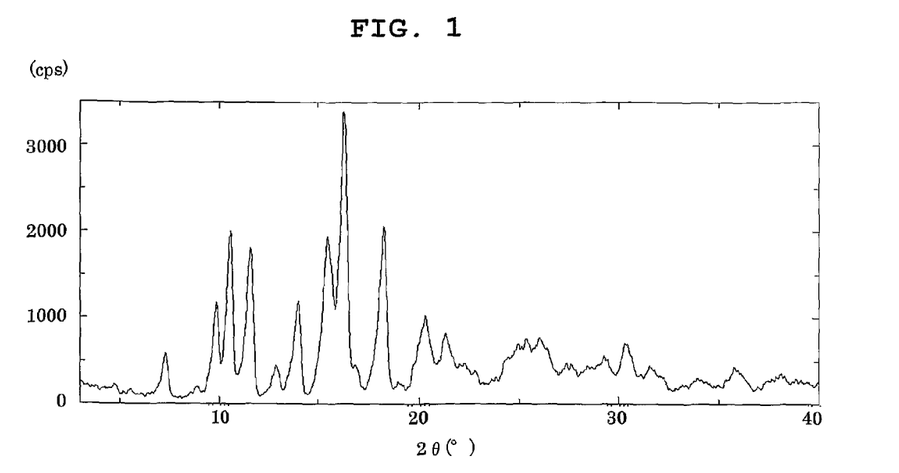
FIG. 1 is one example of a powder X-ray diffraction chart showing the crystal of Reference Example 1.

Preparation of (R)-2-[[[3-methyl-4-(2,2,2-trifluoroethoxy)-2-pyridyl]methyl]sulfinyl]benzimidazole 1.5 hydrate Under a nitrogen atmosphere, 2-[[[3-methyl-4-(2,2,2-trifluoroethoxy)-2-pyridyl]methyl]thio]benzimidazole (100 g), toluene (500 mL), water (0.23 mL) and diethyl (+)-tartrate (10.6 mL) were mixed. Under a nitrogen atmosphere, titanium (IV) isopropoxide (8.3 mL) was added to the mixture at 50° C. to 60° C., and the mixture was stirred at the same temperature for 30 min. Under a nitrogen atmosphere, diisopropylethylamine (16.3 mL) was added to the obtained mixture at 0° C. to 10° C., cumene hydroperoxide (156.8 mL, content 82%) was added at −10° C. to 10° C., and the mixture was stirred at −10° C. to 10° C. for 4 hr to give a reaction mixture. 25% Aqueous sodium thiosulfate solution (135 g) was added to ½ of the reaction mixture under a nitrogen atmosphere to decompose remaining cumene hydroperoxide. The mixture was concentrated to 230 mL, diisopropyl ether (900 mL) was added to the obtained concentrate at room temperature, and the mixture was stirred at the same temperature to allow crystal precipitation. The crystals were separated and washed successively with diisopropyl ether/n-heptane (1/1) (100 mL) and municipal water (100 mL×2) (pale-yellowish white crystals, 101.6 g). The total amount of the wet crystal was dissolved in acetone (200 mL), and the mixture was stirred for 13 min. To a mixture of acetone (75 mL) and municipal water (375 mL) was added dropwise the acetone solution over 17 min, and municipal water (525 mL) was added dropwise over 15 min. After cooling to 10° C. or below, the mixture was stirred for about 2 hr. The crystals were collected by filtration, washed with cooled acetone/municipal water (1/5, 100 mL), and then with municipal water (100 mL) to give pale-yellowish white crystals (103.2 g) of (R)-2-[[[3-methyl-4-(2,2,2-trifluoroethoxy)-2-pyridyl]methyl]sulfinyl]benzimidazole 1.5 hydrate.

Reference Example 2

Figure 2:
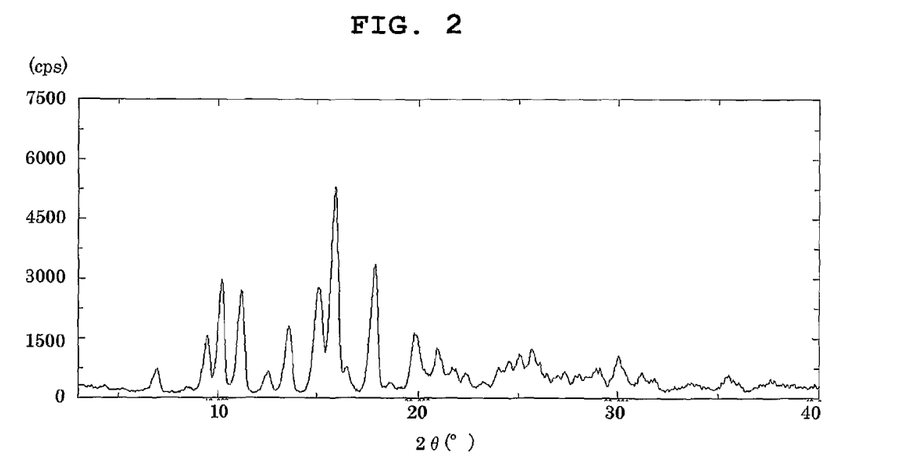
FIG. 2 is one example of a powder X-ray diffraction chart showing the crystal of Reference Example 2.

Preparation of (R)-2-[[[3-methyl-4-(2,2,2-trifluoroethoxy)-2-pyridyl]methyl]sulfinyl]benzimidazole 1.5 hydrate (R)-2-[[[3-Methyl-4-(2,2,2-trifluoroethoxy)-2-pyridyl]methyl]sulfinyl]benzimidazole (40 g) was dissolved in acetone (180 mL). Activated carbon (2.0 g) was added to the solution, and the mixture was stirred for 30 min. Activated carbon was filtered off, and the residue was washed with acetone (20 mL). The obtained mother washing solution was added dropwise to a mixture of acetone (55 mL) and purified water (270 mL) over 9 min. Then, purified water (340 mL) was added dropwise over 18 min. The obtained mixture was cooled to 0° C. to 10° C. and stirred for about 2.5 hr. The crystals were collected by filtration and washed with acetone/purified water (1/5, 90 mL), and then with purified water (90 mL×2) (pale greenish white crystals, 73.9 g). The total amount of the obtained crystal was dissolved in acetone (180 mL), and the activated carbon treatment similar to the above was performed twice (2.0 g of activated carbon was used, respectively). The obtained mother washing solution was added dropwise to a mixture of acetone (55 mL) and purified water (270 mL) over 5 min, and purified water (340 mL) was added dropwise over 9 min. The obtained mixture was cooled to 0° C. to 10° C. and stirred for about 2.5 hr. The crystals were collected by filtration and washed with acetone/purified water (1/5, 90 mL), and then with purified water (90 mL×2) to give (R)-2-[[[3-methyl-4-(2,2,2-trifluoroethoxy)-2-pyridyl]methyl]sulfinyl]benzimidazole 1.5 hydrate crystals (pale-greenish white crystals, 76.0 g).

Reference Example 3

Figure 3:
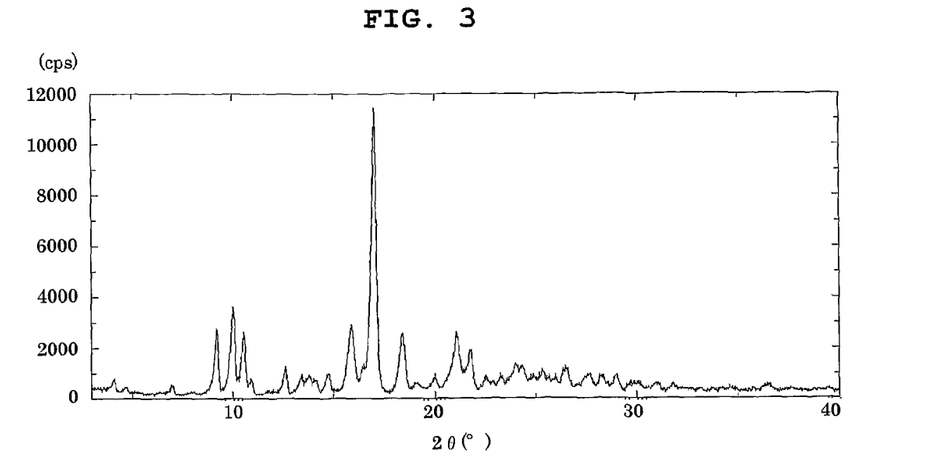
FIG. 3 is one example of a powder X-ray diffraction chart showing the crystal of Reference Example 3.

Preparation of (R)-2-[[[3-methyl-4-(2,2,2-trifluoroethoxy)-2-pyridyl]methyl]sulfinyl]benzimidazole 0.5 hydrate Under a nitrogen atmosphere, 2-[[[3-methyl-4-(2,2,2-trifluoroethoxy)-2-pyridyl]methyl]thio]benzimidazole (100 g), toluene (400 mL), water (0.25 mL) and diethyl (+)-tartrate (10.6 mL) were mixed. Under a nitrogen atmosphere, titanium(IV) isopropoxide (8.3 mL) was added to the mixture at 50° C. to 60° C., and the mixture was stirred at the same temperature for 30 min. Under a nitrogen atmosphere, diisopropylethylamine (16.3 mL) was added to the obtained mixture at 0° C. to 10° C., cumene hydroperoxide (156.8 mL, content 82%) was added at −10° C. to 10° C., and the mixture was stirred at −10° C. to 10° C. for 3 hr to give a reaction mixture. To the reaction mixture was added 25% aqueous sodium thiosulfate solution (393 g) under a nitrogen atmosphere to decompose remaining cumene hydroperoxide. To the mixture was added dibutyl ether (1.8 L) at room temperature, and the mixture was stirred at the same temperature to allow crystal precipitation. The mixture was cooled to −10° C. to 0° C. and stirred. The crystals were separated, and successively washed with dibutyl ether (200 mL) cooled to −10° C. to 0° C. and municipal water (200 mL×2) (yellowish white crystals, 206.9 g). The wet crystals (205.9 g) were dissolved in acetone (398 mL), and the mixture was stirred for 9 min. To a mixture of acetone (149 mL) and municipal water (746 mL) was added dropwise the acetone solution over 10 min, and municipal water (1045 mL) was added dropwise over 20 min. After stirring at room temperature, the crystals were collected by filtration and washed with acetone/municipal water (1/5, 199 mL), and then with municipal water (199 mL) to give pale-yellowish white crystals (181.4 g) of (R)-2-[[[3-methyl-4-(2,2,2-trifluoroethoxy)-2-pyridyl]methyl]sulfinyl]benzimidazole 1.5 hydrate. The wet crystals (180.4 g) were dissolved in acetone (396 mL), and the mixture was stirred for 18 min. To a mixture of acetone (148 mL) and municipal water (742 mL) was added dropwise the acetone solution over 10 min, and municipal water (1039 mL) was added dropwise over 21 min. After stirring at room temperature, the crystals were collected by filtration and washed with acetone/municipal water (1/5, 198 mL), and then with municipal water (198 mL×2) to give pale-yellowish white crystals (144.8 g) of (R)-2-[[[3-methyl-4-(2,2,2-trifluoroethoxy)-2-pyridyl]methyl]sulfinyl]benzimidazole 1.5 hydrate. The crystals (20 g) were dried under reduced pressure at room temperature to give pale-yellowish white crystals (14.2 g) of (R)-2-[[[3-methyl-4-(2,2,2-trifluoroethoxy)-2-pyridyl]methyl]sulfinyl]benzimidazole 0.5 hydrate.

Reference Example 4

Figure 4:
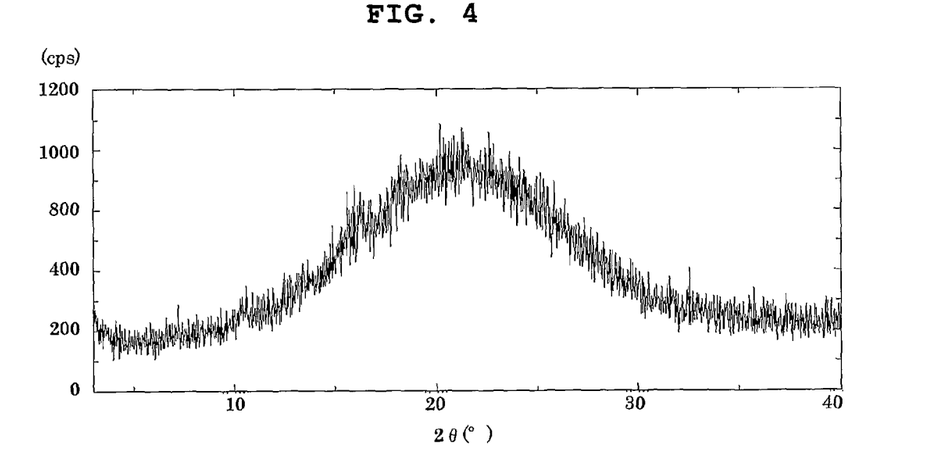
FIG. 4 is one example of a powder X-ray diffraction chart showing the amorphous of Reference Example 4.

Preparation of amorphous (R)-2-[[[3-methyl-4-(2,2,2-trifluoroethoxy)-2-pyridyl]methyl]sulfinyl]benzimidazole (R)-2-[[[3-Methyl-4-(2,2,2-trifluoroethoxy)-2-pyridyl]methyl]sulfinyl]benzimidazole (26 g) was dissolved in acetone (120 mL). The obtained solution was added dropwise to a mixture of acetone (35 mL) and purified water (175 mL) over 9 min. Then, purified water (221 mL) was added dropwise over 5 min. The obtained mixture was cooled to 0° C. to 10° C., and stirred for about 1.5 hr. The crystals were collected by filtration and washed with acetone/purified water (1/5, 60 mL) cooled to 0° C. to 10° C., and then with purified water (60 mL×2) (pale-yellowish white crystals, 50.9 g). The obtained crystals (23.3 g) were dried under reduced pressure at 65° C. for about 9.5 hr to give amorphous (R)-2-[[[3-methyl-4-(2,2,2-trifluoroethoxy)-2-pyridyl]methyl]sulfinyl]benzimidazole (light-brownish white amorphous form, 11.5 g).

Reference Example 5

Figure 5:
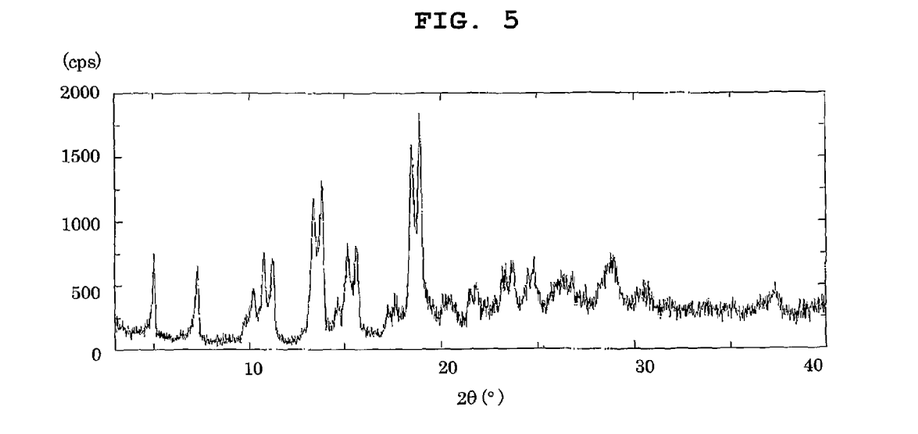
FIG. 5 is one example of a powder X-ray diffraction chart showing the crystal of Reference Example 5.

Preparation of (R)-2-[[[3-methyl-4-(2,2,2-trifluoroethoxy)-2-pyridyl]methyl]sulfinyl]benzimidazole 1.5 hydrate Under a nitrogen atmosphere, 2-[[[3-methyl-4-(2,2,2-trifluoroethoxy)-2-pyridyl]methyl]thio]benzimidazole (43.2 g), toluene (175 mL), water (72.6 mg) and (+)-diethyl tartrate (4.6 mL) were mixed. Under a nitrogen atmosphere, titanium (IV) isopropoxide (3.6 mL) was added to the mixture at 50° C. to 60° C., and the mixture was stirred at the same temperature for 30 min. Under a nitrogen atmosphere, diisopropylethylamine (7.0 mL) was added to the obtained mixture at 15° C. to 25° C., cumene hydroperoxide (65 mL, content 82%) was added at −4° C. to 10° C., and the mixture was stirred at −4° C. to 10° C. for about 4 hr to give a reaction mixture. To the reaction mixture was added 25% aqueous sodium thiosulfate solution (170 g) under a nitrogen atmosphere to decompose remaining cumene hydroperoxide. Dibutyl ether (778 mL) was added to the mixture at room temperature, and the mixture was stirred at the same temperature to allow crystal precipitation. The mixture was cooled to 0° C. to 10° C. and stirred, the crystals were separated and successively washed with dibutyl ether (86 mL) cooled to 0° C. to 10° C. and municipal water (86 mL×2) (yellowish white crystals, 72 g). The wet crystals were dissolved in acetone (173 mL), and the mixture was stirred for about 30 min. To a mixture of acetone (65 mL) and municipal water (324 mL) was added dropwise the acetone solution over 10 min, and then municipal water (454 mL) was added dropwise over 20 min. After stirring at room temperature, the crystals were collected by filtration and washed with acetone/municipal water (1/5, 86 mL), and then with municipal water (43 mL) to give pale-yellowish white crystals (87 g) of (R)-2-[[[3-methyl-4-(2,2,2-trifluoroethoxy)-2-pyridyl]methyl]sulfinyl]benzimidazole 1.5 hydrate. The wet crystals were dissolved in acetone (173 mL), and the mixture was stirred for about 30 min. To a mixture of acetone (65 mL) and municipal water (324 mL) were added dropwise the acetone solution over about 10 min and then municipal water (454 mL) was added dropwise over about 20 min. After stirring at room temperature, the crystals were collected by filtration and washed with acetone/municipal water (1/5, 86 mL), and then with municipal water (43 mL×2) to give pale-yellow white crystals (59.8 g) of (R)-2-[[[3-methyl-4-(2,2,2-trifluoroethoxy)-2-pyridyl]methyl]sulfinyl]benzimidazole 1.5 hydrate.

Example 1

Figure 6:
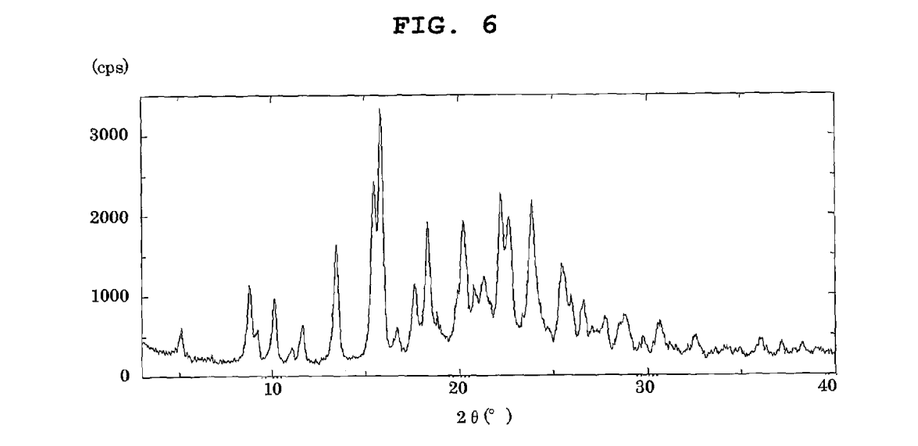
FIG. 6 is one example of a powder X-ray diffraction chart showing the crystal of Example 1.

The wet crystals (6.9 g) obtained in Reference Example 1 were dried under reduced pressure at 90° C. for 1.5 hr to give (R)-2-[[[3-methyl-4-(2,2,2-trifluoroethoxy)-2-pyridyl]methyl]sulfinyl]benzimidazole (brown crystals, 2.9 g).

$^1$H-NMR: 2.23 (3H, s), 4.37 (2H, q, J=7.8 Hz), 4.77 (1H, d, J=13.7 Hz), 4.87 (1H, d, J=13.7 Hz), 6.67 (1H, d, J=5.7 Hz), 7.26-7.33 (2H, m), 7.45 (1H, bs), 7.78 (1H, bs), 8.34 (1H, d, J=5.6 Hz)

IR (vcm$^{-1}$): 3072, 2968, 1577, 1475, 1442, 1311, 1261, 1167 water content: 0.39% optical purity: 99.9% ee chemical purity: 97.9% (285 nm, HPLC area percent value)

melting point (DSC): 148.9° C.

TABLE 1

| 2-θ (°) | XRPD data d-value (Å) | Relative intensity (%) |
|---|---|---|
| 8.880 | 9.9500 | 35 |
| 10.220 | 8.6482 | 32 |
| 13.520 | 6.5438 | 54 |
| 15.540 | 5.6975 | 82 |
| 17.940 | 5.5554 | 100 |
| 17.700 | 5.0068 | 39 |
| 18.440 | 4.8075 | 65 |
| 20.000 | 4.4359 | 36 |
| 20.300 | 4.3710 | 64 |
| 20.900 | 4.2468 | 37 |
| 21.320 | 4.1641 | 41 |
| 21.440 | 4.1411 | 42 |
| 22.320 | 3.9798 | 74 |
| 22.760 | 3.9038 | 71 |

TABLE 1-continued

| 2-θ (°) | XRPD data d-value (Å) | Relative intensity (%) |
|---|---|---|
| 23.840 | 3.7293 | 67 |
| 23.960 | 3.7109 | 74 |
| 24.320 | 3.6568 | 35 |
| 25.540 | 3.4848 | 49 |
| 25.980 | 3.4268 | 34 |
| 26.680 | 3.3385 | 33 |

Example 2

Figure 7:
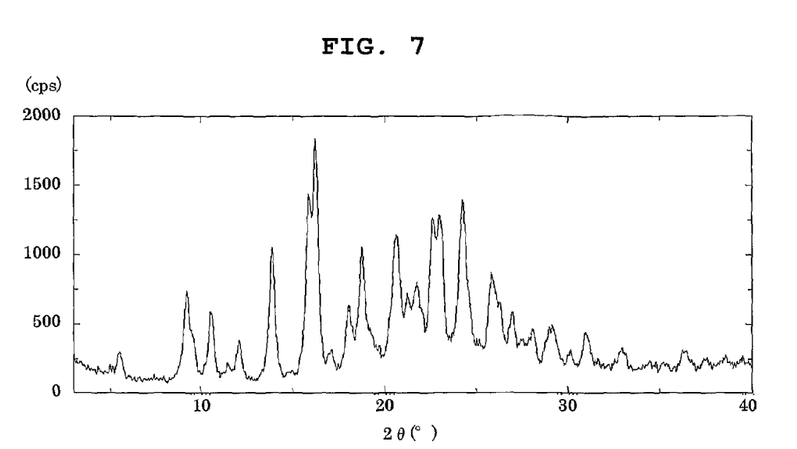
FIG. 7 is one example of a powder X-ray diffraction chart showing the crystal of Example 2.

The wet crystals (7.0 g) obtained in Reference Example 1 were dried under reduced pressure at 100° C. for about 3 hr to give (R)-2-[[[3-methyl-4-(2,2,2-trifluoroethoxy)-2-pyridyl]methyl]sulfinyl]benzimidazole (blackish brown crystals, 2.9 g).

water content: 0.33% chemical purity: 96.1% (285 nm, HPLC area percent value)

TABLE 2

| 2-θ (°) | XRPD data d-value (Å) | Relative intensity (%) |
|---|---|---|
| 8.880 | 9.9500 | 33 |
| 9.260 | 9.5425 | 19 |
| 10.240 | 8.6314 | 27 |
| 11.740 | 7.5317 | 19 |
| 13.540 | 6.5342 | 56 |
| 15.540 | 5.6975 | 79 |
| 15.940 | 5.5554 | 100 |
| 16.660 | 5.3169 | 13 |
| 17.620 | 5.0293 | 28 |
| 17.700 | 5.0068 | 36 |
| 17.780 | 4.9844 | 35 |
| 17.940 | 4.9403 | 18 |
| 18.380 | 4.8230 | 60 |
| 18.480 | 4.7972 | 64 |
| 18.880 | 4.6964 | 23 |
| 19.340 | 4.5857 | 18 |
| 19.520 | 4.5439 | 11 |
| 19.940 | 4.4491 | 26 |
| 20.280 | 4.3753 | 59 |
| 20.400 | 4.3498 | 63 |
| 20.780 | 4.2711 | 22 |
| 20.980 | 4.2308 | 32 |
| 21.420 | 4.1449 | 41 |
| 21.880 | 4.0588 | 19 |
| 22.330 | 3.9833 | 70 |
| 22.760 | 3.9038 | 71 |
| 23.200 | 3.8308 | 16 |
| 23.400 | 3.7985 | 19 |
| 23.600 | 3.7667 | 19 |
| 23.960 | 3.7109 | 68 |

Example 3

Figure 8:
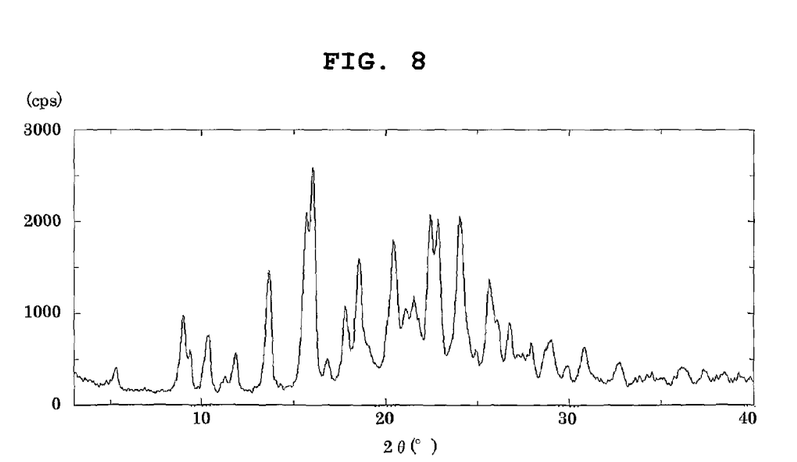
FIG. 8 is one example of a powder X-ray diffraction chart showing the crystal of Example 3.

The wet crystals (30.4 g) obtained in Reference Example 2 were dried under reduced pressure at 90° C. for about 1.5 hr to give (R)-2-[[[3-methyl-4-(2,2,2-trifluoroethoxy)-2-pyridyl]methyl]sulfinyl]benzimidazole (brown crystals, 14.7 g).

water content: 0.19% chemical purity: 99.8% (285 nm, HPLC area percent value)

TABLE 3

| 2-θ (°) | XRPD data d-value (Å) | Relative intensity (%) |
|---|---|---|
| 5.080 | 17.3812 | 10 |
| 8.800 | 10.0403 | 36 |
| 9.200 | 9.6046 | 16 |
| 10.140 | 8.7163 | 28 |
| 11.620 | 7.6092 | 19 |
| 13.440 | 6.5826 | 56 |
| 15.440 | 5.7342 | 75 |
| 15.820 | 5.5973 | 100 |
| 16.680 | 5.3106 | 17 |
| 17.560 | 5.0464 | 32 |
| 17.660 | 5.0180 | 37 |
| 18.340 | 4.8335 | 62 |
| 18.800 | 4.7162 | 22 |
| 19.840 | 4.4713 | 21 |
| 20.220 | 4.3881 | 57 |
| 20.320 | 4.3667 | 51 |
| 20.920 | 4.2428 | 30 |
| 21.220 | 4.1835 | 27 |
| 21.340 | 4.1603 | 31 |
| 21.700 | 4.0920 | 22 |
| 22.240 | 3.9939 | 61 |
| 22.680 | 3.9174 | 60 |
| 23.280 | 3.8178 | 14 |
| 23.820 | 3.7324 | 62 |
| 23.940 | 3.7140 | 50 |
| 24.780 | 3.5900 | 12 |
| 25.440 | 3.4983 | 39 |
| 25.540 | 3.4848 | 33 |
| 25.960 | 3.4294 | 27 |
| 26.500 | 3.3607 | 22 |

Example 4

Figure 9:
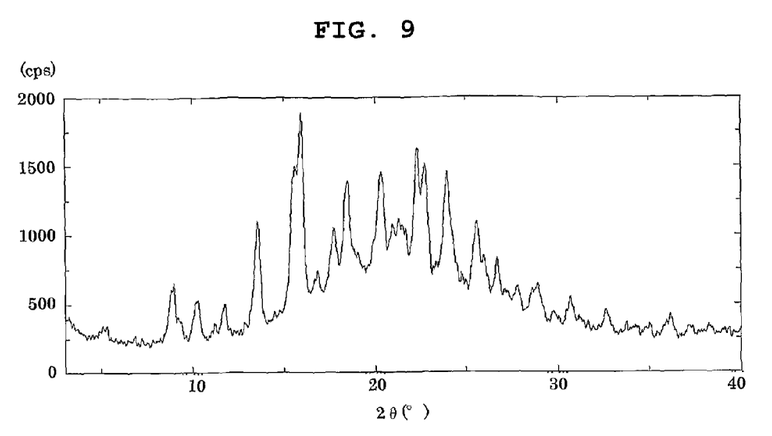
FIG. 9 is one example of a powder X-ray diffraction chart showing the crystal of Example 4.

The wet crystals (30.4 g) obtained in Reference Example 3 were heated at an outer temperature of about 80° C. for about 1.5 hr to give (R)-2-[[[3-methyl-4-(2,2,2-trifluoroethoxy)-2-pyridyl]methyl]sulfinyl]benzimidazole (brown crystals, 14.7 g).

water content: 0.19%

TABLE 4

| 2-θ (°) | XRPD data d-value (Å) | Relative intensity (%) |
|---|---|---|
| 8.840 | 9.9949 | 33 |
| 8.980 | 9.8394 | 35 |
| 10.300 | 8.5812 | 28 |
| 13.540 | 6.5342 | 59 |
| 15.440 | 5.7342 | 72 |
| 15.600 | 5.6757 | 79 |
| 15.960 | 5.5485 | 100 |
| 16.620 | 5.3296 | 35 |
| 16.820 | 5.2667 | 39 |
| 17.320 | 5.1157 | 36 |
| 17.720 | 5.0012 | 57 |
| 18.480 | 4.7972 | 74 |
| 19.060 | 4.6525 | 48 |
| 19.380 | 4.5764 | 41 |
| 19.600 | 4.5255 | 41 |
| 19.880 | 4.4624 | 51 |
| 20.360 | 4.3582 | 78 |
| 20.960 | 4.2348 | 58 |
| 21.320 | 4.1641 | 60 |
| 21.700 | 4.0920 | 56 |
| 22.320 | 3.9798 | 87 |
| 22.780 | 3.9004 | 80 |
| 23.200 | 3.8308 | 41 |
| 23.980 | 3.7079 | 78 |
| 24.540 | 3.6245 | 42 |
| 24.780 | 3.5900 | 40 |
| 25.000 | 3.5589 | 37 |
| 25.600 | 3.4768 | 58 |
| 25.980 | 3.4268 | 45 |
| 26.220 | 3.3960 | 37 |

Example 5

Figure 10:
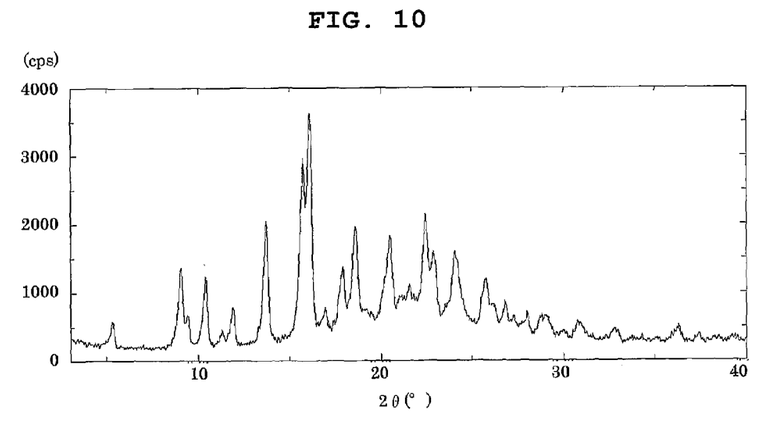
FIG. 10 is one example of a powder X-ray diffraction chart showing the crystal of Example 5.

The amorphous form (1.27 g) obtained in Reference Example 4 was heated at an outer temperature of about 80° C. for about 2 hr (light-brown crystals, 1.24 g).

TABLE 5

| 2-θ (°) | XRPD data d-value (Å) | Relative intensity (%) |
|---|---|---|
| 5.040 | 17.5191 | 11 |
| 8.600 | 10.2733 | 16 |
| 8.740 | 10.1091 | 33 |
| 9.120 | 9.6887 | 18 |
| 10.080 | 8.7680 | 26 |
| 11.580 | 7.6354 | 18 |
| 13.400 | 6.6022 | 57 |
| 15.380 | 5.7564 | 74 |
| 15.780 | 5.6114 | 100 |
| 16.520 | 5.3616 | 11 |
| 16.640 | 5.3232 | 15 |
| 17.580 | 5.0407 | 36 |
| 17.820 | 4.9733 | 15 |
| 18.280 | 4.8492 | 63 |
| 18.740 | 4.7312 | 18 |
| 18.880 | 4.6964 | 15 |
| 19.220 | 4.6141 | 16 |
| 19.800 | 4.4802 | 23 |
| 20.180 | 4.3967 | 60 |
| 20.680 | 4.2915 | 23 |
| 20.840 | 4.2589 | 29 |
| 21.240 | 4.1796 | 34 |
| 21.540 | 4.1221 | 23 |
| 22.160 | 4.0081 | 65 |
| 22.620 | 3.9277 | 59 |
| 23.360 | 3.8049 | 18 |
| 23.800 | 3.7355 | 59 |
| 24.500 | 3.6304 | 9 |
| 24.700 | 3.6014 | 12 |
| 25.320 | 3.5146 | 29 |

Example 6

Figure 11:
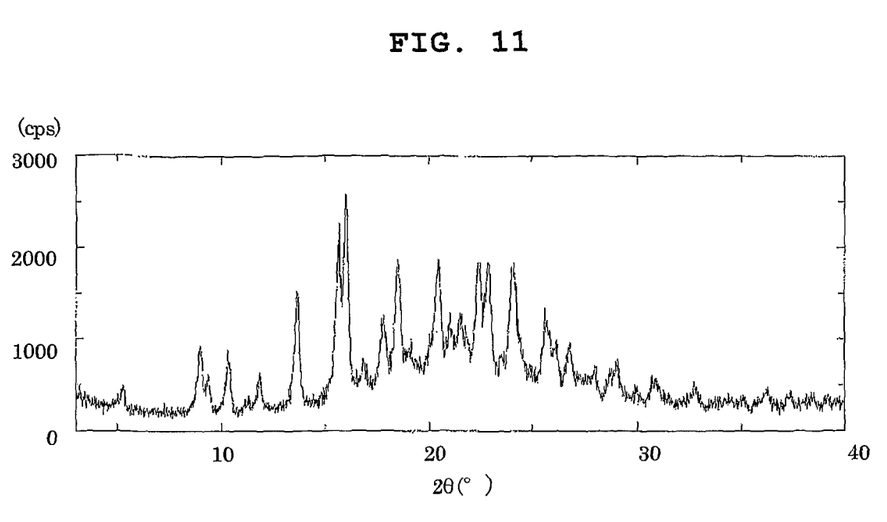
FIG. 11 is one example of a powder X-ray diffraction chart showing the crystal of Example 6.

The wet crystals (25.2 g) obtained in Reference Example 5 were dried under reduced pressure at about 80° C. for about 3.5 hr to give (R)-2-[[[3-methyl-4-(2,2,2-trifluoroethoxy)-2-pyridyl]methyl]sulfinyl]benzimidazole (blackish brown crystals, 20.7 g).

Analytical Example 1

Stability Test

The crystals obtained in Example 6 were placed in a brown glass bottle, preserved at 40° C. for 2 weeks, and the residual rate of the crystal was measured after the preservation (residual rate: 100.7%).

Analytical Example 2

Solubility Test

To the crystals (8.87 mg) obtained in Example 6 was gradually added dropwise an aqueous solution with pH 6.9. The crystals were almost dissolved at the time point when 35 mL was added (solubility: 0.25 mg/mL).

Analytical Example 3

Solubility Test

To the crystals (10.75 mg) obtained in Example 6 was gradually added dropwise an aqueous solution with pH 9.2. The crystals were almost dissolved at the time point when 13.5 mL was added (solubility: 0.80 mg/mL).

INDUSTRIAL APPLICABILITY

Since the crystal of the present invention is superior in the antiulcer activity, gastric acid secretion-inhibitory action, mucosa-protecting action, anti-*Helicobacter pylori* activity and the like, and has low toxicity, it is useful as a pharmaceutical product.

This application is based on patent application No. 059342/2008 filed in Japan, the contents of which are hereby incorporated by reference.

The invention claimed is:

1. A crystal of (R)-2-[[[3-methyl-4-(2,2,2-trifluoroethoxy)-2-pyridinyl]methyl]sulfinyl]-1H-benzimidazole wherein the powder X-ray diffraction analysis pattern has characteristic peaks at interplanar spacings (d) of 10.06±0.2, 8.70±0.2, 6.57±0.2, 5.59±0.2 and 4.00±0.2 Angstrom.

2. A pharmaceutical agent comprising the crystal of claim 1.

3. The pharmaceutical agent of claim 2, which is an agent for the prophylaxis or treatment of peptic ulcer, Zollinger-Ellison syndrome, gastritis, reflux esophagitis, symptomatic gastroesophageal reflux disease (Symptomatic GERD), Barrett's esophagus, functional dyspepsia, gastric cancer, stomach MALT lymphoma, ulcer caused by a nonsteroidal anti-inflammatory agent, or hyperacidity or ulcer due to postoperative stress; or an inhibitor of upper gastrointestinal hemorrhage due to peptic ulcer, acute stress ulcer, hemorrhagic gastritis or invasive stress.

4. A method of treating or preventing peptic ulcer, Zollinger-Ellison syndrome, gastritis, reflux esophagitis, symptomatic gastroesophageal reflux disease (Symptomatic GERD), Barrett's esophagus, functional dyspepsia, gastric cancer, stomach MALT lymphoma, ulcer caused by a nonsteroidal anti-inflammatory agent, or hyperacidity or ulcer due to postoperative stress, which comprises administering an effective amount of the crystal of claim 1 to a mammal.

5. A method of inhibiting upper gastrointestinal hemorrhage due to peptic ulcer, acute stress ulcer, hemorrhagic gastritis or invasive stress, which comprises administering an effective amount of the crystal of claim 1 to a mammal.

6. A production method of a crystal of (R)-2-[[[3-methyl-4-(2,2,2-trifluoroethoxy)-2-pyridinyl]methyl]sulfinyl]-1H-benzimidazole, comprising heating amorphous (R)-2-[[[3-methyl-4-(2,2,2-trifluoroethoxy)-2-pyridinyl]methyl] sulfinyl]-1H-benzimidazole or a solvate crystal of (R)-2-[[[3-methyl-4-(2,2,2-trifluoroethoxy)-2-pyridinyl]methyl] sulfinyl]-1H-benzimidazole to not lower than about 71° C.

* * * * *